United States Patent
Mussmann et al.

(10) Patent No.: US 11,104,867 B2
(45) Date of Patent: *Aug. 31, 2021

(54) DISHWASHING LIQUID HAVING BLEACHING CATALYST AND PROTEASE

(71) Applicant: Henkel AG & Co. KGaA, Duesseldorf (DE)

(72) Inventors: Nina Mussmann, Willich (DE); Thomas Eiting, Duesseldorf (DE); Thorsten Bastigkeit, Wuppertal (DE); Konstantin Benda, Mettmann (DE); Hendrik Hellmuth, Darmstadt (DE); Thomas Weber, Dormagen (DE)

(73) Assignee: HENKEL IP & HOLDING GMBH, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/398,558

(22) Filed: Jan. 4, 2017

(65) Prior Publication Data

US 2017/0114302 A1    Apr. 27, 2017

Related U.S. Application Data

(63) Continuation of application No. 14/102,801, filed on Dec. 11, 2013, now abandoned, which is a continuation of application No. PCT/EP2012/061244, filed on Jun. 14, 2012.

(30) Foreign Application Priority Data

Jun. 16, 2011  (DE) .................. 10 2011 118 037.4

(51) Int. Cl.
   C11D 3/39       (2006.01)
   C11D 11/00      (2006.01)
   C12N 9/50       (2006.01)
   C11D 3/386      (2006.01)
   C11D 17/00      (2006.01)

(52) U.S. Cl.
   CPC .......... C11D 3/38609 (2013.01); C11D 3/386 (2013.01); C11D 3/38618 (2013.01); C11D 3/3932 (2013.01); C11D 3/3942 (2013.01); C11D 11/0023 (2013.01); C11D 17/0047 (2013.01); C12N 9/50 (2013.01); C12Y 304/00 (2013.01)

(58) Field of Classification Search
   CPC ....................................... C12N 9/50
   USPC ........................................ 435/212
   See application file for complete search history.

(56) References Cited

U.S. PATENT DOCUMENTS

| | | | |
|---|---|---|---|
| 4,421,664 A * | 12/1983 | Anderson | C11D 3/0042 252/186.26 |
| 5,153,161 A * | 10/1992 | Kerschner | B01J 31/1805 252/186.38 |
| 5,244,594 A * | 9/1993 | Favre | C11D 3/3932 252/186.21 |
| 6,001,639 A | 12/1999 | Schulein et al. | |
| 6,361,989 B1 | 3/2002 | Svendsen et al. | |
| 6,399,557 B2 | 6/2002 | Perkins et al. | |
| 6,417,151 B1 | 7/2002 | Grothus et al. | |
| 6,589,747 B2 | 7/2003 | Lee et al. | |
| 7,041,488 B2 | 5/2006 | Outtrup et al. | |
| 7,262,042 B2 * | 8/2007 | Weber | C12N 9/48 |
| 7,300,782 B2 | 11/2007 | Breves et al. | |
| 7,449,187 B2 * | 11/2008 | Weber | A61K 8/66 424/184.1 |
| 7,510,859 B2 | 3/2009 | Wieland et al. | |
| 2002/0037824 A1 | 3/2002 | Smets et al. | |
| 2003/0092097 A1 | 5/2003 | Andersen et al. | |
| 2004/0259222 A1 | 12/2004 | Breves et al. | |
| 2007/0128129 A1 | 6/2007 | Stehr et al. | |
| 2008/0145353 A1 | 6/2008 | Amin et al. | |
| 2009/0170745 A1 | 7/2009 | Merkel et al. | |
| 2009/0275493 A1 | 11/2009 | Siegert et al. | |
| 2012/0172280 A1 | 7/2012 | Knotzel et al. | |
| 2012/0252106 A1 | 10/2012 | Knotzel et al. | |
| 2013/0005637 A1 * | 1/2013 | Siegert | C11D 3/386 510/392 |

FOREIGN PATENT DOCUMENTS

| | | | | |
|---|---|---|---|---|
| DE | 102006022216 A1 | 11/2007 | | |
| EP | 0476257 A1 | 3/1992 | | |
| EP | 1305432 B1 | 9/2010 | | |
| WO | 92/06165 A1 | 4/1992 | | |
| WO | 97/08281 A1 | 3/1997 | | |
| WO | 97/14804 A1 | 4/1997 | | |
| WO | 97/22681 A1 † | 6/1997 | | |
| WO | 2007/006305 A1 | 1/2007 | | |
| WO | 2007/079938 A2 | 7/2007 | | |
| WO | 2009/021867 A2 | 2/2009 | | |
| WO | 2011/036263 A1 | 3/2011 | | |
| WO | 2011/036264 A1 † | 3/2011 | | |
| WO | WO2011110625 * | 9/2011 | ............... C12N 9/54 |

OTHER PUBLICATIONS

Siegert et al, 2011; WO2011110625, machine English translation.*
SEQ ID No. 2 herein, BLAST alignment with SEQ ID No. 2 of SIEGERT et al, 2011 (WO2011110625).*
Jorgensen et al., "Cloning and Sequencing of an Alkaline Protease Gene from Bacillus lentus and Amplification of the Gene on the B. lentus Chromosome by an Improved Technique", Applied and Environmental Microbiology, vol. 66, No. 2, pp. 825-827, 2000.

(Continued)

Primary Examiner — Sheridan Swope
(74) Attorney, Agent, or Firm — Lorenz & Kopf, LLP

(57) ABSTRACT

In a dishwashing liquid, the cleaning performance, in particular on bleachable stains such as, for example, tea stains, is to be improved. This succeeds using a dishwashing liquid which comprises a hydrogen peroxide source, a bleaching catalyst and a protease that, in native electrophoresis on a polyacrylamide gel, has a migration distance that is longer than the migration distance of the protease as per SEQ ID NO. 1.

5 Claims, No Drawings

Specification includes a Sequence Listing.

(56) References Cited

OTHER PUBLICATIONS

Guo et al., "Protein Tolerance to Random Amino Acid Change", Proceedings of the National Academy of Sciences of the United States of America, vol. 101, No. 25, pp. 9205-9210, 2004.
PCT International Search Report (PCT/EP2012/061244) dated Sep. 14, 2012.
Gornall et al., "Determination of Serum Proteins by Means of the Biuret Reaction", Journal of Biological Chemistry, vol. 177, pp. 751-766, 1948.
Altschul et al.: "Basic Local Alignment Search Tool" Journal of Molecular Biology, vol. 215, pp. 403-410, 1990.
Altschul et al.: "Gapped BLAST and PSI-BLAST: a New Generation of Protein Database Search Programs", Nucleic Acids Research, vol. 25, No. 17, pp. 3389-3402, 1997.
Notredame et al.: "T-Coffee: A Novel Method for Fast and Accurate Multiple Sequence Alignment", Journal of Molecular Biology, vol. 302, pp. 205-217, 2000.
Chenna et al.: "Multiple Sequence Alignment with the Clustal Series of Programs", Nucleic Acids Research vol. 31, No. 13, pp. 3497-3500, 2003.
"Native PAGE, Separation Technique File No. 120, PhastSystem TM", Amersham Biosciences, 1998.
Davis, "Disc Electrophoresis-II: Method and Application to Human Serum Proteins", Annals New York Academy of Sciences, pp. 404-427, 1964.
Andrews, "Polyacrylamide Gel Electrophoresis. Molecular Weight Measurement and the Use of Gel Concentration Gradients", Electrophoresis. Theory, Techniques, and Biochemical and Clinical Applications, Second Edition, Food Research Institute, Clarendon Press, pp. 93-116, 1986.
Hames, "An Introduction to Polyacrylamide Gel Electrophoresis", Gel Electrophoresis of Proteins: A Practical Approach, IRL Press Limited, pp. 4-14, 1981.

\* cited by examiner
† cited by third party

DISHWASHING LIQUID HAVING BLEACHING CATALYST AND PROTEASE

CROSS-REFERENCE TO RELATED APPLICATIONS

The present application is a continuation of U.S. Ser. No. 14/102,801, filed Dec. 11, 2013 and entitled "DISHWASHING LIQUID HAVING BLEACHING CATALYST AND PROTEASE", which is a continuation of International Patent Application No. PCT/EP2012/061244, filed Jun. 14, 2012, which claims priority to DE 10 2011 118 037.4, filed Jun. 16, 2011, by which all are hereby incorporated by reference in their entirety.

FIELD OF THE INVENTION

The present invention generally relates to dishwashing agents, and more particularly relates to bleach-containing dishwashing agents that comprise proteases, as well as to methods, in which such agents are used. The invention further relates to uses of such agents.

BACKGROUND OF THE INVENTION

Dishwashing agents are available to the consumer in numerous presentation forms. Besides the traditional liquid hand dishwashing agents, the automatic dishwashing agents in particular have become highly important as a result of the growing use of automatic dishwashers. These automatic dishwashing agents are typically offered to the consumer in solid form, for example as a powder or as tablets.

One of the main aims of the manufacturer of automatic cleaning agents is to improve the cleaning performance of these agents, wherein recently greater emphasis has been focused on the cleaning performance in low temperature cleaning cycles or in cleaning cycles with a reduced water consumption.

Bleachable stains, especially tea stains, represent intractable stains, however, which are often not satisfactorily removed. Modern dishwashing agents, especially automatic dishwashing agents, often do not satisfy the set requirements in regard to the elimination of such stains. Consequently, there is still a need for dishwashing agents and among these especially automatic dishwashing agents, which reliably remove bleachable stains, particularly even at lower cleaning temperatures.

In this regard, the European Patent application EP 846155 discloses that the action of bleaching agents on tea stains is increased by adding lipases. The use of amino acids as bleach stabilizers emerges from the European Patent application EP 476257. An improved bleaching power by combining defined proteases and bleach catalysts is not found in the prior art.

Accordingly, it is desirable to provide dishwashing agents with an improved cleaning power for bleachable stains, especially tea stains.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A dishwashing agent containing a hydrogen peroxide source, a bleach catalyst and a protease, characterized in that the protease in a native electrophoresis in a polyacrylamide gel has a migration distance that is longer than the migration distance of the protease according to SEQ ID NO: 1.

A method for removing stains, in particular tea stains, on hard surfaces, in particular dishes, said method comprising one of the procedural steps (a) contacting the hard surface with a cleaning liquor that comprises a dishwashing agent according to one of claims 1 to 8, or (b) contacting the hard surface with a cleaning liquor that comprises a hydrogen peroxide source, a bleach catalyst and a protease, wherein the protease in a native electrophoresis in a polyacrylamide gel has a migration distance that is longer than the migration distance of the protease according to SEQ ID NO: 1.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Subject matter of the invention is a dishwashing agent comprising a hydrogen peroxide source, a bleach catalyst and a protease, wherein the protease in a native electrophoresis in a polyacrylamide gel has a migration distance that is longer than the migration distance of the protease according to SEQ ID NO: 1.

It has surprisingly been determined that these kinds of dishwashing agents that comprise such proteases combined with a bleach catalyst possess a very good bleaching power and consequently exhibit a very good cleaning power for bleachable stains, especially tea stains. In preferred developments of the agent according to the invention, there consequently exists a synergy between the relevant protease and the bleach catalyst in regard to the cleaning power, especially in regard to the cleaning power for tea stains. Further preferred developments of the agent according to the invention exhibit such advantageous cleaning powers even at low temperatures and/or in short wash cycles. In the context of the invention, a low temperature is preferably between 10° C. and 50° C., preferably between 15° C. and 45° C. and particularly preferably between 20° C. and 40° C. A short wash cycle preferably lasts 60 minutes at most, 45 minutes or only 30 minutes at most. Further preferred developments of the agent according to the invention exhibit an improved rinsing performance.

The cleaning power describes the ability of a dishwashing agent, especially an automatic dishwashing agent, to partially or totally remove an existing stain. In the context of the invention, both the dishwashing agent that contains the protease or the dishwashing agent liquor formed by this agent, as well as the protease itself, has a particular cleaning power. Therefore the cleaning power of the enzyme contributes to the cleaning power of the agent and the cleaning liquor formed by the agent.

Cleaning liquor is understood to mean that working solution comprising the dishwashing agent and which acts on the hard surfaces and thus comes into contact with the stains present on the hard surfaces. The cleaning liquor is usually formed when the cleaning process begins and the dishwashing agent is diluted with water, for example in a dishwasher or in another suitable vessel.

The inventively employed protease possesses an increased net charge over the protease of SEQ ID NO: 1. The net charge of the protease essentially determines its migration distance in electrophoresis, in particular also in a native electrophoresis in a polyacrylamide gel. In a native electrophoresis in a polyacrylamide gel, inventively employed proteases exhibit a migration distance that is longer than the migration distance of the protease of SEQ ID NO: 1.

Here, the migration distance of a protease in a native polyacrylamide gel is a parameter that takes into account and sums up the significant characteristics of the protease, in particular the net charge, but also additional characteristics, such as for example structural characteristics of the tertiary structure, amino acid composition and/or additional charge characteristics (e.g. isoelectric point). Consequently, this parameter also reflects the increased net charge of an inventively employed protease with respect to the net charge of the protease according to SEQ ID NO: 1.

Surprisingly, it is exactly those proteases that can be defined by their increased migration distance over a subtilisin according to SEQ ID NO: 1 established in the prior art and employed in washing and cleaning agents. These proteases in combination with the bleach catalyst in an agent according to the invention bring about an improved cleaning power on bleachable stains, in particular tea stains. In this regard there preferably exists a synergistic interaction. SEQ ID NO. 1 is the amino acid sequence of subtilisin 309 that already exhibits a high migration distance and/or a high net charge lower than the proteases established in the prior art and employed in washing and cleaning agents. The advantageous interaction with the bleach catalyst consequently occurs in such proteases that in comparison to the already high migration distance of subtilisin 309 exhibit an even higher migration distance, for example due to their charge characteristics and/or structural and/or biochemical characteristics.

In preferred developments, in a native electrophoresis in a polyacrylamide gel, the inventively employed protease exhibits a migration distance that corresponds to at least 1.05 times the migration distance of the protease of SEQ ID NO: 1. In a native electrophoresis in a polyacrylamide gel, the protease increasingly preferably exhibits a migration distance that corresponds to at least 1.06 times, 1.07 times, 1.08 times, 1.09 times and particularly preferably 1.1 times the migration distance of the protease of SEQ ID NO: 1. In a native electrophoresis in a polyacrylamide gel, those proteases are likewise preferred that exhibit a migration distance that corresponds to at least 1.12 times, 1.13 times, 1.14 times, 1.15 times, 1.16 times, 1.17 times, 1.18 times, 1.19 times, and 1.2 times the migration distance of the protease of SEQ ID NO: 1.

The migration distance is determined by native polyacrylamide electrophoresis, a standard biochemical method that is known to the person skilled in the field of enzyme technology. In this regard, the polyacrylamide gel preferably contains a separation gel and a stacking gel, wherein the separation of the proteins in the separation gel (at pH 6.4) defines the migration difference. For focusing the samples, a stacking gel, in which the protein samples are focused at pH 8.8, is preferably upstream from the separation gel. The basic proteins, in particular the inventively specified proteases, are separated in the reversed polarity electrode mode (i.e. with a polarity that is reversed with respect to the usual polarity in polyacrylamide gel electrophoreses), such that the positively charged proteins migrate through the gel in the direction of the negatively charged electrode. The electrophoresis is continued until the protein band that is the protease according to SEQ ID NO: 1 has covered at least half of the available path length, preferably at least two thirds of the available path length in the separation gel, unless the band that is the inventively employed protease had already reached the end of the gel. In such a case the electrophoresis is continued until the inventively employed protease has covered at least half of the available path length, preferably at least two thirds of the available path length in the separation gel The proteases in the gel can be detected using a customary gel stain, for example with Coomassie-Brilliant Blue dye or silver stain. This procedure permits an exact determination of the migration distance of the inventively employed protease against the migration distance of the protease according to SEQ ID NO: 1. The migration distance is the path length, measured (in the direction of electrophoresis) from the beginning of the separation gel to the position of the relevant protease band in the separation gel. It is important that both proteins are subjected to the same native polyacrylamide gel electrophoresis, such that the relative migration behavior of both proteins to one another is measured in the same experiment.

The migration distance is quite particularly preferably measured using the PHASTSystem of GE Healthcare. Native polyacrylamide "PhastGel Gradient 8-25" gels were used as the separation gel with a size of at least 43×50×0.45 mm, in combination with a 0.112M Tris, 0.112M acetate (pH 6.4) buffer. "Native buffer strips" of 3% agarose were used as the stacking gel with a size of at least 41×10×6 mm, in combination with a 0.25M Tris, 0.88ML alanine (pH 8.8) buffer. The separation was carried out as in "PhastSystem Separation Technique File No. 120" (Amersham Biosciences 1998), but in the "reversed polarity electrode mode" for the separation of basic proteins. In this regard we refer explicitly to this reference (cf. the supplementary publications by Davis, B. J., "Disc Electrophoresis II: Methods and Application to human serum proteins", Ann. N.Y. Acad. p. 121 (1964), pp. 404-427, by Andrews, A. T. (Editors Peacocke, A. R. and Harrington, W. F.), "Molecular weight measurement and the use of gel concentration gradients", in "Electrophoresis. Theory, techniques and biochemical and clinical applications", Clarendon Press, Oxford, 1981, pp. 63-80, and flames, B. D. (Editors Harnes, B. D. and Rickwood, D.), "An introduction to Polyacrylamide gel electrophoresis", in "Gel electrophoresis of proteins: A practical approach", IRL Press Limited, London, Washington D.C., 1981, pp. 4-14).

A dishwashing agent according to the invention comprises the protease with increasing preference in an amount of $1\times10^{-8}$ to 10 wt %, of 0.00001 to 2 wt %, of 0.001 to 1 wt %, of 0.007 to 0.8 wt %, of 0.025 to 0.5 wt % and particularly preferably 0.04 bis 0.38 wt %, based on the total protein content of the protease. The protein concentration can be determined using known methods, for example the BCA Process (bicinchoninic acid; 2,2'-biquinolyl-4,4'-dicarboxylic acid) or the biuret process (A. G. Gornall, C. S. Bardawill and M. M. David, J. Biol. Chem., 177 (1948), pp. 751-766).

The protease can also be adsorbed on carriers and/or embedded in encapsulants, in order to protect them against premature inactivation. In the cleaning liquor, i.e. under conditions of use, the enzyme is then released and can develop its catalytic activity.

A dishwashing agent according to the invention further comprises a bleach catalyst. These substances are preferably bleach-boosting transition metal salts or transition metal complexes such as, for example, manganese-, iron-, cobalt-, ruthenium- or molybdenum-salen or -carbonyl complexes. Manganese, iron, cobalt, ruthenium, molybdenum, titanium, vanadium and copper complexes with nitrogen-containing tripod ligands, as well as cobalt-, iron-, copper- and ruthenium-ammine complexes may also be employed as the bleach catalysts.

Complexes of manganese in the valence state II, III, IV or V which preferably comprise one or a plurality of macrocyclic ligands with the donor functions N, NR, PR, O and/or S are particularly preferably employed. Ligands having nitrogen donor functions are preferably employed. In this regard, it is particularly preferred to incorporate bleach catalyst(s) into the compositions according to the invention, which comprise 1,4,7-trimethyl-1,4,7-triazacyclononane (Me-TACN), 1,4,7-triazacyclononane (TACN), 1,5,9-trimethyl-1,5,9-triazacyclododecane (Me-TACD), 2-methyl-1,4,7-trimethyl-1,4,7-triazacyclononane (Me/Me-TACN) and/or 2-methyl-1,4,7-triazacyclononane (Me/TACN) as the macromolecular ligands. Suitable manganese complexes are for example $[Mn^{III}_2(\mu\text{-}O)_1(\mu\text{-}OAc)_2(TACN)_2](ClO_4)_2$, $[Mn^{III}Mn^{IV}(\mu\text{-}O)_2(\mu\text{-}OAc)_1(TACN)_2](BPh_4)_2$, $[Mn^{IV}_4(\mu\text{-}O)_6(TACN)_4](ClO_4)_4$, $[Mn^{III}_2(\mu\text{-}O)_1(\mu\text{-}OAc)_2(Me\text{-}TACN)_2](ClO_4)_2$, $[MN^{III}Mn^{IV}(\mu\text{-}O)_1(\mu\text{-}OAc)_2(Me\text{-}TACN)_2](ClO_4)_3$, $[Mn^{IV}_2(\mu\text{-}O)_3(Me\text{-}TACN)_2](PF_6)_2$ and $[Mn^{IV}_2(\mu\text{-}O)_3(Me\text{-}TACN)_2](PF_6)_2$ ($OAc=OC(O)CH_3$).

Dishwashing agents, in particular automatic dishwashing agents, characterized in that it comprises a bleach catalyst selected from the group of the bleach boosting transition metal salts and transition metal complexes, preferably from the group of the complexes of manganese with 1,4,7-trimethyl-1,4,7-triazacyclononane (Me-TACN) or 1,2,4,7-tetramethyl-1,4,7-triazacyclononane (Me/Me-TACN), are preferred according to present invention, as these cited bleach catalysts can particularly contribute to a significantly improved cleaning result.

The abovementioned bleach boosting transition metal complexes, in particular with the central atoms Mn and Co, are preferably employed in an amount of up to 5 wt %, particularly from 0.0025 wt % to 1 wt % and particularly preferably from 0.01 wt % to 0.30 wt %, each relative to the total weight of the bleach catalyst-containing agent. However, in special cases more bleach activator may also be employed.

A dishwashing agent according to the invention further comprises a hydrogen peroxide source. These sources concern compounds that supply, or can supply, $H_2O_2$ in water. The hydrogen peroxide source preferably concerns a bleaching agent, wherein oxygen bleaching agents are preferred according to present invention.

Sodium percarbonate, sodium perborate tetrahydrate and sodium perborate monohydrate are of particular importance among the compounds that serve as bleaching agents and liberate $H_2O_2$ in water. Examples of additional bleaching agents that may be used are peroxypyrophosphates, citrate perhydrates and $H_2O_2$-liberating peracidic salts or peracids, such as perbenzoates, peroxyphthalates, diperoxyazelaic acid, phthaloimino peracid or diperoxydodecanedioic acid.

Moreover, bleaching agents from the group of the organic bleaching agents can also be employed. Typical organic bleaching agents are the diacyl peroxides, such as e.g. dibenzoyl peroxide. Further typical organic bleaching agents are the peroxy acids, wherein the alkylperoxy acids and the arylperoxy acids may be named as examples.

The hydrogen peroxide source is preferably comprised in an amount of 2-30 wt % and increasingly preferably in 4-25 wt %, in 5-20 wt % and particularly preferably in 6-15 wt % in the dishwashing agent according to the invention, each relative to the total weight of the dishwashing agent. Preferred dishwashing agents are those wherein the dishwashing agent comprises, each relative to the total weight of the dishwashing agent, 2 to 20 wt %, preferably 3 to 18 wt % and particularly 4 to 15 wt % of sodium percarbonate.

Consequently, particularly preferred embodiments of the dishwashing agents according to the invention are those, wherein the bleach catalyst is selected from the group of the bleach boosting transition metal salts and transition metal complexes, preferably from the group of the complexes of manganese with 1,4,7-trimethyl-1,4,7-triazacyclononane Me-TACN) or 1,2,4,7-tetramethyl-1,4,7-triazacyclononane (Me/Me-TACN), and/or the hydrogen peroxide source is sodium percarbonate, sodium perborate tetrahydrate or sodium perborate monohydrate or a combination thereof. The bleach catalyst is quite particularly preferably a complex of manganese with 1,4,7-trimethyl-1,4,7-triazacyclononane (Me-TACN), in particular $[Mn^{IV}_2(\mu\text{-}O)_3(Me\text{-}TACN)_2](PF_6)_2$, or 1,2,4,7-tetramethyl-1,4,7-triazacyclononane (Me/Me-TACN) or a mixture therefrom, and the hydrogen peroxide source sodium percarbonate. The bleach catalyst and the hydrogen peroxide source in the cited combinations are each preferably present in of the abovementioned quantities.

Dishwashing agents according to the invention, in particular automatic dishwashing agents, can further comprise bleach activators, for example in order to achieve an improved bleach activity when cleaning at temperatures of 60° C. and below. Bleach activators, which can be employed, are compounds which, under perhydrolysis conditions, yield aliphatic peroxycarboxylic acids having preferably 1 to 10 carbon atoms, in particular 2 to 4 carbon atoms, and/or optionally substituted perbenzoic acid. Substances, which carry O-acyl and/or N-acyl groups of said number of carbon atoms and/or optionally substituted benzoyl groups, are suitable. Polyacylated alkylenediamines are preferred, tetraacetyl ethylenediamine (TAED) having proven to be particularly suitable.

These bleach activators, especially TAED, are preferably employed in amounts of 0.1-10 wt %, particularly 0.1-8 wt %, especially 2-8 wt % and particularly preferably 2-6 wt %, each relative to the total weight of the bleach activator-containing agent.

In another preferred embodiment of the invention, the calculated isoelectric point of the protease in the dishwashing agent is greater than 9.3 and increasingly preferably greater than 9.33, 9.37, 9.4, 9.43, 9.47 and 9.5 and/or the calculated net charge of the protease is greater than 3.38 and increasingly preferably greater than 3.4, 3.5, 3.6, 3.7, 3.8, 3.9, 4, 4.1, 4.2, 4.3 and 4.35. It has been shown that these types of protease in combination with the bleach catalyst in an agent according to the invention afford a particularly advantageous cleaning power on bleachable stains, in particular tea stains. In a native electrophoresis in a polyacrylamide gel, these types of proteases furthermore exhibit a migration distance that is longer than the migration distance of the protease according to SEQ ID NO: 1. In this regard, the isoelectric point and the net charge are preferably calculated by means of the "Analysis" function of the BioAnnotater module of the software packet Vector NTI® Advance 10.3.0 (Invitrogen Corporation, 1600 Faraday Avenue, Carlsbad, Calif., USA) with the predefined standard (default) parameters.

Alternatively or in addition, the protease comprises an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequence listed in SEQ ID NO: 3, or comprises an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequence listed in SEQ ID NO: 2, or comprises an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence listed in SEQ ID NO: 1.

The protease particularly preferably comprises an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequence listed in SEQ ID NO: 3. A protease according to SEQ ID NO. 3 is quite particularly preferred.

The identity of nucleic acid or amino acid sequences is determined by a sequence comparison. This comparison is made by aligning similar sequences in the nucleotide sequences or amino acid sequences with one another. This sequence comparison is preferably carried out based on the BLAST algorithm that is established in the prior art and usually used (see for example Altschul, S. F., Gish, W., Miller, W., Myers, E. W. & Lipman, D. J. (1990) "Basic local alignment search tool." J. Mol. Biol. 215: 403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, pp. 3389-3402) and does so principally by aligning similar sequences of nucleotides or amino acids in the nucleic acid sequences or amino acid sequences with one another. A tabular assignment of the positions is called the alignment. Another algorithm that is available from the prior art is the FASTA algorithm. Sequence alignments, particularly multiple sequence alignments, are usually created with computer programs. The Clustal series are frequently used (see for example Chenna et al. (2003): Multiple sequence alignment with the Clustal series of programs, Nucleic Acid Research 31, 3497-3500), T-Coffee (see, for example Notredame et al. (2000): T-Coffee: A novel method for multiple sequence alignments. J. Mol. Biol. 302, 205-217) or programs that are based on these programs or algorithms. In the context of the present invention, sequence comparisons and alignments were preferably created with the software packet Vector NTI® Advance 10.3.0 (Invitrogen Corporation, 1600 Faraday Avenue, Carlsbad, Calif., USA) with the standard default parameters.

A comparison of this type allows a statement to be made of the similarity of the compared sequences to one another. It is usually expressed in percent identity, i.e. in the fraction of the identical nucleotides or amino acid residues to the same positions or in an alignment to one another in corresponding positions. The wider term "homology" for amino acid sequences takes into consideration conserved amino acid exchanges, i.e. amino acids with similar chemical activity, as they exercise mostly similar activities or functions within the protein. Consequently, the similarity of the compared sequences can also be expressed as percent homology or percent similarity. Identity and/or homology data can be gathered for complete polypeptides or genes or only for individual areas. Homologous or identical areas of various nucleic acid or amino acid sequences are therefore defined by matches in the sequences. They often possess the same or similar functions. They can be small and include only a few nucleotides or amino acids. It is frequently the case that such small areas execute essential functions for the total activity of the protein. Consequently, it can be worthwhile to obtain sequence matches only for individual, optionally small areas. However, when not otherwise stated, identity or homology data in the present application refer to the total length of the relevant listed nucleic acid or amino acid sequence.

In a preferred embodiment of the invention, a dishwashing agent according to the invention concerns an automatic dishwashing agent. In accordance with this application, compositions are designated as automatic dishwashing agents which can be employed in an automatic dishwashing process for cleaning soiled dishes. Thus the automatic dishwashing agents according to the invention differ for example from the automatic rinsing agents that are always employed in combination with automatic dishwashing agents and develop no inherent cleaning action.

Nowadays, more stringent standards are often posed for machine-washed tableware than for hand-washed tableware. Thus, the tableware should not only be free of food residues after the automatic dishwashing, but should also for example not have any whitish blemishes from water hardness or other mineral salts that originate from dried water droplets due to a lack of wetting agent. Modern automatic dishwashing agents meet these requirements by incorporating cleaning and/or caring and/or water softening and/or rinsing active agents and are known to the consumer as for example "2 in 1" or "3 in 1" dishwashing agents. The automatic dishwashing agents comprise builders as the essential component for the successful cleaning and rinsing. Firstly, these builders increase the alkalinity of the cleaning liquor, wherein with an increasing alkalinity fats and oils are emulsified and saponified, and secondly, reduce the water hardness of the cleaning liquor by complexing the calcium ions contained in the aqueous liquor.

In another embodiment of the invention, the dishwashing agent is in solid form. This is understood to mean all solid presentation forms, for example powders, granulates or extrudates.

A powdery agent according to the invention can exist for example as a free-flowing powder, in particular with a bulk density of 300 g/l to 1200 g/l, especially 500 g/l to 900 g/l or 600 g/l to 850 g/l.

The dishwashing agent according to the invention, in particular the automatic dishwashing agents, are preferably in the form of a molded object, in particular a compacted material, principally a tablet. For the molded object, however, it can also be a granulate for example that is comprised in a bag or in a cast shape.

Agents according to the invention can be presented as one-phase or multi-phase products. Automatic dishwashing agents, in particular with one, two, three or four phases, are preferred. Automatic dishwashing agents in the form of a prefabricated unit dose with two or more phases are particularly preferred. In particular, tablets with two or more phases are particularly preferred, for example two-layer tablets, in particular two-layer tablets with a recess and a molded object in the recess.

Automatic dishwashing agents according to the invention are preferably prefabricated as unit doses. These unit doses preferably contain the necessary quantity of washing or cleaning active substances for one cleaning cycle. Preferred unit doses weigh between 12 and 30 g, preferably between 14 and 26 g and especially between 15 and 22 g.

The volume of the abovementioned unit doses and their three-dimensional shape are particularly preferably chosen such that the prefabricated units can be dosed by being placed in the dosing chamber of a dishwasher. Consequently, the volume of the unit dose is preferably between 10 and 35 ml, preferably between 12 and 30 ml and especially between 15 and 25 ml.

The automatic dishwashing agents according to the invention, in particular the prefabricated unit doses, have, in a preferred embodiment, a water-soluble coating.

The manufacture of the solid agent according to the invention presents no difficulties and can be effected by known methods, for example by spray drying or granulation, wherein enzymes and possible further heat-sensitive ingredients, such as, for example bleaching agent are optionally subsequently added separately. For manufacturing the inventive agent with an increased bulk density, particularly in the range of 650 g/l to 950 g/l, a preferred process is one with an extrusion step.

The manufacture of the molded body according to the invention, in particular the cleaning agent tablets, is preferably carried in a manner known to the person skilled in the art by compressing particulate starting materials. To produce the tablets, the premix is compacted in a so-called die between two punches to form a solid core. This operation, which hereinafter is abbreviated to tableting, is divided into four steps: metering, compaction (elastic deformation), plastic deformation, and ejection. Rotary presses are preferably used for the tableting.

When tableting with rotary presses, it has been found advantageous to perform tableting with minimal fluctuations in tablet weight. Fluctuations in tablet hardness can also be reduced in this way. Minimal fluctuations in weight can be achieved in the following manner:

Using plastic inserts with small thickness tolerances
Low rotational speed of the rotor
Large feed shoe
Matching the rpm of the feed shoe impeller to that of the rotor
Feed shoe with constant powder height
Decoupling the feed shoe from the powder drum The ingredients intended for tableting can be filled simultaneously into the die in the form of a common particulate premix or filled sequentially in the form of individual, separate powders or granulates or simultaneously into the die, wherein the dosing of a prefabricated particulate premix is preferred.

It was surprisingly found that the granulates employed to manufacture the molded object can be compressed particularly well. Thus, by preferably using a compression force of 40 to 65 kN, particularly preferably 48 to 60 kN, cores can be obtained with a hardness in the range of 150 to 250 N, in particular in the range of 200 to 230 N, and moreover have particularly good free flowing characteristics. Accordingly, the granulates can be compressed preferably with a relatively low compression force to cores with relatively high hardness, which moreover preferably have very good free flowing characteristics. Correspondingly, the other way round, it is advantageous that for manufacturing cores of lower hardness, preferably a lower compression force has to be used than for manufacturing conventional cores.

In another preferred embodiment, compositions according to the invention, in particular molded objects, comprise polyvinyl pyrrolidone particles. These particles facilitate inter alia the disintegration of the molded objects and insofar act as disintegration auxiliaries or tablet disintegrants. It has proven to be inventively particularly advantageous to employ polyvinyl pyrrolidone particles with an average particle size of 100 to 150 μm, in particular with an average particle size of 110 to 130 μm.

The term "average particle size" or "average size" in the context of the present invention is understood to mean the volume average $D_{50}$ particle size that can be measured using conventional methods. The $D_{50}$ volume average particle size is that point in the particle size distribution, at which 50 vol % of the particles have a smaller diameter and 50 vol % of the particles have a larger diameter. The average particle size can be measured in particular with the help of dynamic light scattering, which is usually carried out on dilute suspensions that comprise e.g. 0.01 to 1 wt % of particles.

It is particularly preferred when the PVP particles not only exhibit an average particles size of 100 to 150 μm, in particular 110 to 130 μm, but moreover that the particle size of the added particles is preferably completely within the cited ranges. This is ensured by employing particle size fractions with the cited particle sizes that were obtained by a sieving method.

The PVP particles are comprised in the compositions according to the invention, in particular in molded objects, preferably in an amount of 0.1 to 5 wt %, in particular in an amount of 0.2 to 3 wt %, above all in an amount of 0.3 to 1.8 wt %.

The action of disintegrants generally consists in that their volume increases on water ingress, wherein firstly they swell, secondly the release of gas can generate a pressure that causes the tablet to disintegrate into smaller particles. In addition to, or as an alternative to the PVP particles, other disintegrants, for example carbonate/citric acid systems or carbonate in combination with other organic acids, synthetic polymers or naturally occurring polymers or modified natural products such as cellulose and starch and their derivatives as well as alginates or casein derivatives can also be comprised in compositions according to the invention, in particular molded objects. Furthermore, gas-evolving effervescent systems can also be employed as additional disintegrants. Preferred effervescent systems consist of at least two ingredients that react together to form a gas, for example alkali metal carbonate and/or -hydrogen carbonate and an acidifying agent capable of releasing carbon dioxide from the alkali metal salts in aqueous solution. One acidifying agent that releases carbon dioxide from the alkali metal salts in aqueous solution is, for example, citric acid.

The additional disintegration auxiliaries, insofar as they are used, are preferably employed in quantities of 0.1 to 10 wt %, advantageously from 0.2 to 5 wt % and especially from 0.5 to 2 wt %, each relative to the total weight of the agent containing the disintegration aid.

In another embodiment of the invention, the dishwashing agent is in the form of a liquid, gel or paste.

All liquid or free-flowing dosage forms can be used as the liquid agent. In the context of the present application, "free-flowing" is understood to mean preparations that are pourable and can have viscosities up to several 10 000 mPas. The viscosity can be measured using standard methods (for example using a Brookfield-Viscosimeter LVT-II at 20 rpm and 20° C., spindle 3) and is preferably in the range of 5 to 10 000 mPas. Preferred agents have viscosities from 10 to 8000 mPas, particularly preferably from 120 to 3000 mPas. In the context of the present invention, a liquid agent can therefore also be in gel form or in paste form, it can be a homogenous solution or suspension, it can be sprayable for example or can be packaged in other usual dosage forms.

Liquid or pasty inventive agents in the form of solutions in standard solvents are generally prepared by a simple mixing of the ingredients, which can be added as is or as a solution into an automatic mixer.

Therefore, embodiments of the present invention further include all solid, powdery, liquid, gellified or pasty presentation forms of the agent which can also optionally consist of a plurality of phases as well as being in a compressed on non-compressed form. An agent according to the invention can also be packaged in a container, preferably an air-permeable container, from which the agent is released shortly before use or during the cleaning procedure.

In another embodiment of the invention, a dishwashing agent according to the invention additionally comprises another ingredient that is selected from the group consisting of builder, surfactant, anionic polymer as well as combinations hereof. In another embodiment of the invention, a dishwashing agent according to the invention is phosphate-free. Phosphate-free dishwashing agents according to the invention are particularly advantageous with respect to environmental considerations.

Preferably, the ingredients of the agent are harmonized with each other. Synergies are preferred in regard to the cleaning power and/or rinsing performance and/or the inhibition of deposits. Particularly preferred synergies are present in a temperature range between 10° C. and 60° C., especially in a temperature range of 10° C. to 50° C., from 10° C. to 40° C., from 10° C. to 30° C., from 15° C. to 30° C., from 10° C. to 25° C. and from 15° C. to 25° C.

The group of preferred builders includes in particular the citrates as well as the carbonates and the organic co-builders. The term "citrate" hereby includes both citric acid as well as its salts, in particular its alkali metal salts. Particularly preferred dishwashing agents according to the invention, in particular automatic dishwashing agents, comprise citric acid and citrate, preferably sodium citrate, in amounts of 5 to 60 wt %, preferably 10 to 50 wt % and particularly 15 to 40 wt %.

Carbonate(s) and/or hydrogen carbonate(s), preferably alkali metal carbonate(s), particularly preferably sodium carbonate, are particularly preferably added in quantities of 5 to 50 wt %, preferably 10 to 40 wt % and especially 15 to 30 wt %, each relative to the weight of the dishwashing agent.

Polycarboxylates/polycarboxylic acids and phosphonates may be particularly mentioned as the organic co-builders. These classes of substances are described below.

Useful organic builders are, for example, the polycarboxylic acids that can be used in the form of the free acid and/or their sodium salts, polycarboxylic acids in this context being understood to be carboxylic acids that carry more than one acid function. These include, for example, adipic acid, succinic acid, glutaric acid, malic acid, tartaric acid, maleic acid, fumaric acid, sugar acids, amino carboxylic acids, nitrilotriacetic acid (NTA) and mixtures thereof. Besides their building effect, the free acids also typically have the property of an acidifying component and hence also serve to establish a relatively low and mild pH of the inventive agents. Succinic acid, glutaric acid, adipic acid, gluconic acid and any mixtures thereof are particularly to be mentioned in this regard.

Besides the 1-hydroxyethane-1,1-diphosphonic acid, the phosphonate complexants include a series of different compounds such as for example diethylenetriamine penta(methylene phosphonic acid) (DTPMP). Hydroxyalkane phosphonates or amino alkane phosphonates are particularly preferred in this application. Among the hydroxyalkane phosphonates, 1-hydroxyethane-1,1-diphosphonate (HEDP) is of particular importance as the cobuilder. It is normally added as the sodium salt, the disodium salt reacting neutral and the tetrasodium salt reacting alkaline (pH 9). Ethylenediamine tetramethylene phosphonate (EDTMP), diethylenetriamine pentamethylene phosphonate (DTPMP) and their higher homologs are preferably chosen as the aminoalkane phosphonates. They are preferably added in the form of the neutral-reacting sodium salts, e.g. as the hexasodium salt of EDTMP or as the hepta and octasodium salt of DTPMP. Of the class of phosphonates, HEDP is preferably used as the builder. The aminoalkane phosphonates additionally possess a pronounced ability to complex heavy metals. Accordingly, it can be preferred, particularly where the agents also contain bleach, to use amino alkane phosphonates, particularly DTPMP, or mixtures of the cited phosphonates.

In the context of this application, a preferred dishwashing agent, in particular an automatic dishwashing agent, comprises one or more phosphonate(s) from the group a) aminotrimethylene phosphonic acid (ATMP) and/or salts thereof;
b) ethylenediamine tetra(methylene phosphonic acid) (EDTMP) and/or salts thereof;
c) diethylenetriamine penta(methylene phosphonic acid) (DTPMP) and/or salts thereof;
d) 1-hydroxyethane-1,1-diphosphonic acid (HEDP) and/or salts thereof;
e) 2-phosphonobutane-1,2,4-tricarboxylic acid (PBTC) and/or salts thereof;
f) hexamethylenediamine tetra(methylene phosphonic acid) (HDTMP) and/or salts thereof;
g) nitrilotri(methylene phosphonic acid) (NTMP) and/or salts thereof.

Particularly preferred automatic dishwashing agents comprise 1-hydroxyethane-1,1-diphosphonic acid (HEDP) or diethylenetriamine penta(methylene phosphonic acid) (DTMP) as the phosphonates.

Of course the dishwashing agents according to the invention, in particular automatic dishwashing agents, can comprise two or more different phosphonates.

The weight fraction of the phosphonates in the total weight of the dishwashing agent according to the invention, in particular the automatic dishwashing agent, is advantageously 1 to 8 wt %, preferably 1.2 to 6 wt % and especially 1.5 to 4 wt %.

The dishwashing agents according to the invention, in particular the automatic dishwashing agents, can comprise one or more surfactants, wherein anionic surfactants, non-ionic surfactants and their mixtures particularly come into question.

Those preferred anionic surfactants possess at least one sulfate or sulfonate group. The anionic surfactant with at least one sulfate or sulfonate group is preferably selected from fatty alcohol sulfates, alkane sulfonates and alkylbenzene sulfonates. $C_{12}$-$C_{18}$ fatty alcohol sulfates (FAS), e.g. Sulfopon K 35 (Cognis, Germany), secondary $C_{13}$-$C_{17}$ alkane sulfonates (SAS), e.g. Hostapur SAS 93 (Clariant, Germany), as well as linear $C_8$-$C_{18}$ alkylbenzene sulfonates, in particular dodecylbenzene sulfonate (LAS) are particularly preferred in this regard.

According to the invention, the terms "sulfate" and "sulfonate" also include, in addition to the anionic compounds in question that are present in the form of salts, the free acids, i.e. the corresponding alkyl sulfur acids or alkyl sulfonic acids.

The anionic surfactant containing at least one sulfate or sulfonate group is preferably comprised in dishwashing agents according to the invention in an amount of 0.1 to 20 wt %, particularly preferably 0.5 to 15 wt %, in particular 2.5 to 10 wt %.

All non-ionic surfactants known to the person skilled in the art can be used as the non-ionic surfactants. Suitable exemplary non-ionic surfactants are alkyl glycosides that satisfy the general Formula RO(G)$_x$, in which R means a primary linear or methyl-branched, particularly 2-methyl-branched, aliphatic group containing 8 to 22 and preferably 12 to 18 carbon atoms and G stands for a glycose unit containing 5 or 6 carbon atoms, preferably glucose. The degree of oligomerization x, which defines the distribution of monoglycosides and oligoglycosides, is any number between 1 and 10, preferably x is 1.2 to 1.4.

Another class of preferred non-ionic surfactants which may be used, either as the sole non-ionic surfactant or in combination with other non-ionic surfactants, are alkoxylated, preferably ethoxylated or ethoxylated and propoxylated fatty acid alkyl esters preferably containing 1 to 4 carbon atoms in the alkyl chain.

Non-ionic surfactants of the amine oxide type, for example N-cocoalkyl-N,N-dimethylamine oxide and N-tallow alkyl-N,N-dihydroxyethylamine oxide, and the fatty acid alkanolamides may also be suitable. The quantity in which these non-ionic surfactants are used is preferably no more than the quantity in which the ethoxylated fatty alcohols are used and, particularly no more than half that quantity.

Other suitable surfactants are polyhydroxyfatty acid amides corresponding to the Formula,

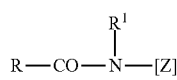

in which R stands for an aliphatic acyl residue with 6 to 22 carbon atoms, R$^1$ for hydrogen, an alkyl or hydroxyalkyl residue with 1 to 4 carbon atoms and [Z] for a linear or branched polyhydroxyalkyl residue with 3 to 10 carbon atoms and 3 to 10 hydroxyl groups. The polyhydroxyfatty acid amides are known substances, which may normally be obtained by reductive amination of a reducing sugar with ammonia, an alkylamine or an alkanolamine and subsequent acylation with a fatty acid, a fatty acid alkyl ester or a fatty acid chloride.

The group of the polyhydroxyfatty acid amides also includes compounds corresponding to the Formula

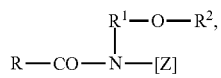

in which R is a linear or branched alkyl or alkenyl group containing 7 to 12 carbon atoms, R$^1$ is a linear, branched or cyclic alkyl residue or an aryl residue containing 2 to 8 carbon atoms and R$^2$ is a linear, branched or cyclic alkyl residue or an aryl residue or an oxyalkyl residue containing 1 to 8 carbon atoms, C$_{1-4}$ alkyl- or phenyl residues being preferred, and [Z] is a linear polyhydroxyalkyl residue, of which the alkyl chain is substituted by at least two hydroxy groups, or alkoxylated, preferably ethoxylated or propoxylated derivatives of that group.

[Z] is preferably obtained by reductive amination of a reducing sugar, for example glucose, fructose, maltose, lactose, galactose, mannose or xylose. The N-alkoxy- or N-aryloxy-substituted compounds may then be converted into the required polyhydroxyfatty acid amides by reaction with fatty acid methyl esters in the presence of an alkoxide as the catalyst.

The preferred surfactants are weakly foaming non-ionic surfactants. Washing or cleaning agents, particularly cleaning agents for dishwashing and among this preferably for automatic dishwashers, are especially preferred when they comprise non-ionic surfactants from the group of the alkoxylated alcohols. Preferred non-ionic surfactants are alkoxylated, advantageously ethoxylated, particularly primary alcohols preferably containing 8 to 18 carbon atoms and, on average, 1 to 12 moles of ethylene oxide (EO) per mole of alcohol, in which the alcohol group may be linear or, preferably, methyl-branched in the 2-position or may contain e.g. linear and methyl-branched residues in the form of the mixtures typically present in Oxo alcohol residues. Particularly preferred are, however, alcohol ethoxylates with linear groups from alcohols of natural origin with 12 to 18 carbon atoms, e.g. from coco-, palm-, tallow- or oleyl alcohol, and an average of 2 to 8 EO per mole alcohol. Exemplary preferred ethoxylated alcohols include C$_{12-14}$ alcohols with 3 EO or 4 EO, C$_{9-11}$ alcohols with 7 EO, C$_{13-15}$ alcohols with 3 EO, 5 EO or 7 EO, C$_{12-18}$ alcohols with 3 EO, 5 EO or 7 EO and mixtures thereof, such as mixtures of C$_{12-14}$ alcohols with 3 EO and C$_{12-18}$ alcohols with 5 EO. The cited degrees of ethoxylation constitute statistically average values that can be a whole or a fractional number for a specific product. Preferred alcohol ethoxylates have a narrowed homolog distribution (narrow range ethoxylates, NRE). In addition to these non-ionic surfactants, fatty alcohols with more than 12 EO can also be used. Examples of these are tallow fatty alcohol with 14 EO, 25 EO, 30 EO or 40 EO.

Accordingly, ethoxylated non-ionic surfactant(s) prepared from C$_{6-20}$ monohydroxy alkanols or C$_{6-20}$ alkylphenols or C$_{12-20}$ fatty alcohols and more than 12 mole, preferably more than 12 mole and especially more than 20 mole ethylene oxide per mole alcohol, are used with particular preference. A particularly preferred non-ionic surfactant is obtained from a straight-chain fatty alcohol containing 16 to 20 carbon atoms (C$_{16-20}$ alcohol), preferably a C$_{18}$ alcohol, and at least 12 moles, preferably at least 15 moles and more preferably at least 20 moles of ethylene oxide. Of these non-ionic surfactants, the so-called narrow range ethoxylates are particularly preferred.

Moreover, surfactant(s) that comprise one or more tallow fat alcohols with 20 to 30 EO in combination with a silicone defoamer are particularly preferably used.

Non-ionic surfactants that have a melting point above room temperature are used with particular preference. Non-ionic surfactant(s) with a melting point above 20° C., preferably above 25° C., particularly preferably between 25 and 60° C. and, especially between 26.6 and 43.3° C., are particularly preferred.

Suitable non-ionic surfactants with a melting and/or softening point in the cited temperature range are, for example weakly foaming non-ionic surfactants that can be solid or highly viscous at room temperature. If non-ionic surfactants are used that are highly viscous at room temperature, then it is preferred that they have a viscosity greater than 20 Pa s, preferably above 35 Pa s and especially above 40 Pa s. Non-ionic surfactants that have a waxy consistency at room temperature are also preferred.

Non-ionic surfactants from the group of the alkoxylated alcohols, particularly preferably from the group of the mixed alkoxylated alcohols and especially from the group of the EO-AO-EO-non-ionic surfactants are likewise incorporated with particular preference.

Preferably, the room temperature solid non-ionic surfactant additionally has propylene oxide units in the molecule. These PO units preferably make up as much as 25% by weight, more preferably as much as 20% by weight and, especially up to 15% by weight of the total molecular weight of the non-ionic surfactant. Particularly preferred non-ionic surfactants are ethoxylated monohydroxyalkanols or alkylphenols, which have additional polyoxyethylene-polyoxypropylene block copolymer units. The alcohol or alkylphenol component of these non-ionic surfactant molecules preferably makes up more than 30 wt %, more preferably more than 50 wt % and most preferably more than 70 wt % of the total molecular weight of these non-ionic surfactants. Preferred compositions are characterized in that they comprise ethoxylated and propoxylated non-ionic surfactants, in which the propylene oxide units in the molecule preferably make up as much as 25% by weight, more preferably as much as 20% by weight and, especially up to 15% by weight of the total molecular weight of the non-ionic surfactant.

Preferred surfactants that are solid at room temperature are used and belong to the groups of the alkoxylated non-ionic surfactants, more particularly the ethoxylated primary alcohols, and mixtures of these surfactants with structurally more complex surfactants, such as polyoxypropylene/polyoxyethylene/polyoxypropylene ((PO/EO/PO) surfactants). Such (PO/EO/PO) non-ionic surfactants are moreover characterized as having good foam control.

Other particularly preferred non-ionic surfactants with melting points above room temperature comprise 40 to 70% of a polyoxypropylene/polyoxyethylene/polyoxypropylene block polymer blend, which comprises 75% by weight of an inverted block copolymer of polyoxyethylene and polyoxypropylene with 17 moles of ethylene oxide and 44 moles of propylene oxide and 25% by weight of a block copolymer of polyoxyethylene and polyoxypropylene initiated with trimethylol propane and comprising 24 moles of ethylene oxide and 99 moles of propylene oxide per mole of trimethylol propane.

Particularly preferred non-ionic surfactants in the context of the present invention have proved to be weakly foaming non-ionic surfactants, which have alternating ethylene oxide and alkylene oxide units. Among these, the surfactants with EO-AO-EO-AO blocks are again preferred, wherein one to ten EO or AO groups respectively are linked together, before a block of the other groups follows. Here, non-ionic surfactants of the general Formula

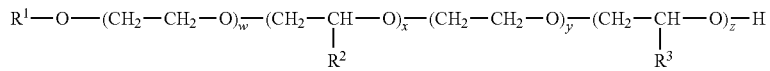

are preferred, in which $R^1$ stands for a linear or branched, saturated or a mono or polyunsaturated $C_{6-24}$ alkyl or -alkenyl group, each group $R^2$ or $R^3$ independently of one another is selected from —$CH_3$, —$CH_2CH_3$, —$CH_2CH_2$—$CH_3$, $CH(CH_3)_2$, and the indices w, x, y, z independently of one another stand for whole numbers from 1 to 6.

The preferred non-ionic surfactants of the previous formula can be manufactured by known methods from the corresponding alcohols $R^1$—OH and ethylene oxide or alkylene oxide. The group $R^1$ in the previous Formula can vary depending on the origin of the alcohol. When natural sources are used, the group $R^1$ has an even number of carbon atoms and generally is not branched, the linear alcohols of natural origin with 12 to 18 carbon atoms, for example coconut, palm, tallow or oleyl alcohol being preferred. The alcohols available from synthetic sources are, for example Guerbet alcohols or mixtures of methyl branched in the 2-position or linear and methyl branched groups, as are typically present in Oxo alcohols. Independently of the type of alcohol used for the manufacture of the non-ionic surfactants comprised in the compositions, non-ionic surfactants are preferred, in which $R^1$ in the previous formula stands for an alkyl group containing 6 to 24, preferably 8 to 20, particularly preferably 9 to 15 and particularly 9 to 11 carbon atoms.

In addition to propylene oxide, especially butylene oxide can be the alkylene oxide unit that alternates with the ethylene oxide unit in the preferred non-ionic surfactants. However, also other alkylene oxides are suitable, in which $R^2$ or $R^3$ independently of one another are selected from —$CH_2CH_2$—$CH_3$ or $CH(CH_3)_2$. Preferably, non-ionic surfactants of the previous formula are used, in which $R^2$ or $R^3$ stand for a group —$CH_3$, w and x independently of one another stand for values of 3 or 4 and y and z independently of one another stand for values of 1 or 2.

In summary, especially non-ionic surfactants are preferred that have a $C_{9-15}$ alkyl group with 1 to 4 ethylene oxide units, followed by 1 to 4 propylene oxide units, followed by 1 to 4 ethylene oxide units, followed by 1 to 4 propylene oxide units. These surfactants exhibit the required low viscosity in aqueous solution and according to the invention are used with particular preference.

Surfactants of the general formula $R^1$—$CH(OH)CH_2O$-$(AO)_w$-$(A'O)_x$-$(A''O)_y$-$(A'''O)_z$—$R^2$, in which $R^1$ and $R^2$ independently of one another stands for a linear or branched, saturated or unsaturated or mono- or polyunsaturated $C_{2-40}$ alkyl or alkenyl residue; A, A', A" and A''' independently of one another stands for a residue from the group —$CH_2CH_2$, —$CH_2CH_2$—$CH_2$, —$CH_2CH(CH_3)$, —$CH_2CH_2$—$CH_2CH_2$, —$CH_2CH(CH_3)$—$CH_2$—, —$CH_2CH(CH_2$—$CH_3)$; and w, x, y and z stand for values between 0.5 and 90, wherein x, y and/or z can also be 0, are inventively preferred.

Quite particularly preferred non-ionic surfactants here are of the general Formula $R^1O[CH_2CH(CH_3)O]_x[CH_2CH_2O]_y$ $[CH_2CH(CH_3)O]_zCH_2$ $CH(OH)R^2$, in which $R^1$ stands for a linear or branched aliphatic hydrocarbon residue with 4 to 22 carbon atoms, particularly 6 to 18 carbon atoms, or mixtures thereof, $R^2$ means a linear or branched hydrocarbon residue with 2 to 26 carbon atoms or mixtures thereof and x and z stand for values between 0 and 40 and y stands for a value of at least 15, preferably 15 to 120, particularly preferably from 20 to 80.

In a preferred embodiment, the dishwashing agent, in particular the automatic dishwashing agent, comprises, relative to its total weight, non-ionic surfactant of the general Formula $R^1O[CH_2CH(CH_3)O]_x[CH_2CH_2O]_y$ $[CH_2CH (CH_3)O]_zCH_2CH(OH)R^2$ in amounts of 0.1 to 15 wt %, preferably 0.2 to 10 wt %, particularly preferably 0.5 to 8 wt % and in particular from 1.0 to 6 wt %.

Those end-blocked poly(oxyalkylated) non-ionic surfactants according to the formula $R^1O[CH_2CH_2O]_yCH_2CH(OH)R^2$ are particularly preferred, in which $R^1$ stands for a linear or branched aliphatic hydrocarbon residue with 4 to 22 carbon atoms, particularly 6 to 18 carbon atoms, or mixtures thereof, $R^2$ means a linear or branched hydrocarbon residue with 2 to 26, especially 4 to 20 carbon atoms or mixtures thereof and y stands for a value between 15 and 120, preferably 20 to 100, in particular 20 to 80. The group of these non-ionic surfactants includes for example hydroxy mixed ethers of the general formula $C_{6-22}$ $CH(OH)CH_2O$-$(EO)_{20-120}$—$C_{2-26}$, for example the $C_{8-12}$ fatty alcohol-$(EO)_{22}$-2-hydroxydecyl ethers and the $C_{4-22}$ fatty alcohol-$(EO)_{40-80}$-2-hydroxyalkyl ethers.

A dishwashing agent according to the invention, in particular an automatic dishwashing agent, wherein a surfactant is employed as the weakly foaming non-ionic surfactant of the general Formula $R^1CH(OH)CH_2O$—$(CH_2CH_2O)_{20-120}$—$R^2$, wherein $R^1$ and $R^2$ independently of one another stand for a linear or branched aliphatic hydrocarbon residue with 2 to 20, particularly 4 to 16 carbon atoms, are particularly preferred.

Further preferred are surfactants of the Formula $R^1O[CH_2CH(CH_3)O]_x[CH_2CH_2O]_yCH_2CH(OH)R^2$, in which $R^1$ stands for a linear or branched aliphatic hydrocarbon residue with 4 to 22 carbon atoms or mixtures thereof, $R^2$ means a linear or branched hydrocarbon residue with 2 to 26 carbon atoms or mixtures thereof and x stands for values between 0.5 and 4, preferably 0.5 to 1.5, and y stands for a value of at least 15.

Further inventively preferred surfactants are also of the general Formula $R^1O[CH_2CH(CH_3)O]_x[CH_2CH_2O]_y[CH_2CH(OH)R^2$, in which $R^1$ stands for a linear or branched aliphatic hydrocarbon group with 4 to 22 carbon atoms or mixtures thereof, $R^2$ means a linear or branched hydrocarbon group with 2 to 26 carbon atoms or mixtures thereof and x stands for values between 1 and 40 and y stands for a value between 15 and 40, wherein the alkylene units $[CH_2CH(CH_3)O]$ and $[CH_2CH_2O]$ are randomized, i.e. exist in the form of a statistical, random distribution.

The group of the preferred end-capped poly(oxyalkylated) non-ionic surfactants also includes non-ionic surfactants of the formula $R^1O[CH_2CH_2O]_x[CH_2CH(R^3)O]_yCH_2CH(OH)R^2$, in which $R^1$ and $R^2$ independently of one another stand for linear or branched, saturated or mono or polyunsaturated hydrocarbon groups containing 2 to 26 carbon atoms, $R^3$ independently of one other is selected from —$CH_3$, —$CH_2CH_3$, —$CH_2CH_2$—$CH_3$, —$CH(CH_3)_2$, preferably, however, stands for —$CH_3$, and x and y independently of one another stand for values between 1 and 32, wherein surfactants with $R^3$=—$CH_3$ and values for x of 15 to 32 and y of 0.5 and 1.5 are quite particularly preferred.

Further preferred employable non-ionic surfactants are the end-capped poly(oxyalkylated) non-ionic surfactants corresponding to the Formula

in which $R^1$ and $R^2$ stand for linear or branched, saturated or unsaturated, aliphatic or aromatic hydrocarbon groups containing 1 to 30 carbon atoms, $R^3$ stands for H or for a methyl, ethyl, n-propyl, isopropyl, n-butyl, 2-butyl or 2-methyl-2-butyl group, x for values between 1 and 30, k and j have values between 1 and 12, preferably between 1 and 5.

Each $R^3$ in the above formula $R^1O[CH_2CH(R^3)O]_x[CH_2]_kCH(OH)[CH_2]_jOR^2$ can be different for the case where x≥2. $R^1$ and $R^2$ are preferably linear or branched, saturated or unsaturated, aliphatic or aromatic hydrocarbon groups containing 6 to 22 carbon atoms, groups containing 8 to 18 carbon atoms being particularly preferred. H, —$CH_3$ or —$CH_2CH_3$ are particularly preferred for the group $R^3$. Particularly preferred values for x are in the range from 1 to 20 and more particularly in the range from 6 to 15.

As described above, each $R^3$ in the above formula can be different for the case where x≥2. By this means, the alkylene oxide unit in the straight brackets can be varied. If, for example, x has a value of 3, then the substituent $R^3$ may be selected to form ethylene oxide ($R^3$=H) or propylene oxide ($R^3$=$CH_3$) units which may be joined together in any order, for example (EO)(PO)(EO), (EO)(EO)(PO), (EO)(EO)(EO), (PO)(EO)(PO), (PO)(PO)(EO) and (PO)(PO)(PO). The value 3 for x was selected by way of example and may easily be larger, the range of variation increasing with increasing x-values and including, for example, a large number of (EO) groups combined with a small number of (PO) groups or vice versa.

Particularly preferred end-capped poly(oxyalkylated) alcohols corresponding to the above formula have values for both k and j of 1, so that the above formula can be simplified to

In this last formula, $R^1$, $R^2$ and $R^3$ are as defined above and x stands for numbers from 1 to 30, preferably 1 to 20 and especially 6 to 18. Surfactants in which the substituents R and $R^2$ have 9 to 14 carbon atoms, $R^3$ stands for H and x assumes values of 6 to 15 are particularly preferred.

Further preferred employable non-ionic surfactants are non-ionic surfactants of
the general formula $R^1O(AlkO)_xM(OAlk)_yOR^2$, wherein $R^1$ and $R^2$ independently of one another stand for a branched or unbranched, saturated or unsaturated, optionally hydroxylated group with 4 to 22 carbon atoms; Alk stands for a branched or unbranched alkyl group with 2 to 4 carbon atoms; x and y independently of one another stand for values between 1 and 70; and M stands for an alkyl group from the group $CH_2$, $CHR^3$, $CR^3R^4$, $CH_2CHR^3$ and $CHR^3CHR^4$, wherein $R^3$ and $R^4$ independently of one another stand for branched or unbranched, saturated or unsaturated alkyl groups with 1 to 18 carbon atoms.

In this respect, non-ionic surfactants are preferred with the general Formula

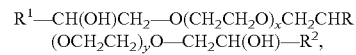

wherein
R, $R^1$ and $R^2$ independently of each other stand for an alkyl group or alkenyl group containing 6 to 22 carbon atoms; x and y independently of one another stand for values between 1 and 40.

In this regard, particularly compounds of the general Formula are preferred:

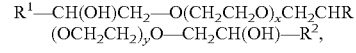

in which R stands for a linear, saturated alkyl group with 8 to 16 carbon atoms, preferably 10 to 14 carbon atoms and n and m independently of one another have values of 20 to 30. Appropriate compounds can be obtained for example by treating alkyl diols HO—CHR—$CH_2$—OH with ethylene oxide, wherein subsequently the free OH functionalities are treated with an alkyl epoxide to afford a dihydroxy ether.

In another preferred embodiment, the non-ionic surfactant is selected from non-ionic surfactants of the general formula $R^1\text{—}O(CH_2CH_2O)_xCR^3R^4(OCH_2CH_2)_yO\text{—}R^2,$ in which
$R^1$ and $R^2$ independently of one another stand for an alkyl group or alkenyl group containing 4 to 22 carbon atoms;
$R^3$ and $R^4$ independently of one another stand for H or an alkyl group or alkenyl group containing 1 to 18 carbon atoms and
x and y independently of one another stand for values between 1 and 40.

In this regard, particularly compounds of the general Formula are preferred:

$R^1\text{—}O(CH_2CH_2O)_xCR^3R^4(OCH_2CH_2)_yO\text{—}R^2,$ in which $R^3$ and $R^4$ stand for H and the indices x and y independently of one another assume values of 1 to 40, preferably from 1 to 15.

In particular, particularly preferred compounds are of the general Formula $R^1\text{—}O(CH_2CH_2O)_xCR^3R^4(OCH_2CH_2)_yO\text{—}R^2,$ in which the $R^1$ and $R^2$ groups independently of one another represent saturated alkyl groups with 4 to 14 carbon atoms and the indices x and y independently of one another assume values of 1 to 15 and especially 1 to 12.

Further preferred compounds are of the general Formula $R^1\text{—}O(CH_2CH_2O)_xCR^3R^4(OCH_2CH_2)_yO\text{—}R^2,$ in which one of the $R^1$ and $R^2$ groups is branched.

Quite particularly preferred compounds are of the general Formula $R^1\text{—}O(CH_2CH_2O)_xCR^3R^4(OCH_2CH_2)_yO\text{—}R^2,$ in which the indices x and y independently of one another assume values from 8 to 12.

The cited carbon chain lengths and degrees of ethoxylation or alkoxylation of the abovementioned non-ionic surfactants constitute statistically average values that can be a whole or a fractional number for a specific product. Due to the manufacturing processes, commercial products of the cited formulas do not consist in the main of one sole representative, but rather are a mixture, wherein not only the carbon chain lengths but also the degrees of ethoxylation or alkoxylation can be average values and thus be fractional numbers.

Of course, the abovementioned non-ionic surfactants can not only be employed as single substances, but also as surfactant mixtures of two, three, four or more surfactants. Accordingly, surfactant mixtures do not refer to mixtures of non-ionic surfactants that as a whole fall under one of the above cited general formulas, but rather refer to such mixtures that comprise two, three, four or more non-ionic surfactants that can be described by the different abovementioned general formulas.

Non-ionic surfactants that have a melting point above room temperature are particularly preferred. Non-ionic surfactant(s) with a melting point above 20° C., preferably above 25° C., particularly preferably between 25 and 60° C. and, especially between 26.6 and 43.3° C., is/are particularly preferred.

In a preferred embodiment, the weight fraction of the non-ionic surfactant in the total weight of the dishwashing agent according to the invention, particularly an automatic dishwashing agent, is 0.1 to 20 wt %, particularly preferably 0.5 to 15 wt %, in particular 2.5 to 10 wt %.

In a preferred embodiment, the wt % ratio of the anionic surfactant with at least one sulfate or sulfonate group to the non-ionic surfactant is from 3:1 to 1:3, especially 2:1 to 1:2, particularly preferably 1.5:1 to 1:1.5.

Dishwashing agents according to the invention, particularly automatic dishwashing agents, comprise in a preferred embodiment at least one anionic polymer as an additional ingredient. In this regard, preferred anionic polymers are the copolymeric polycarboxylates and the copolymeric polysulfonates.

In a preferred embodiment, the weight fraction of the anionic polymer in the total weight of the dishwashing agent according to the invention, particularly in an automatic dishwashing agent, is 0.1 to 20 wt %, preferably 0.5 to 18 wt %, particularly preferably 1.0 to 15 wt % and in particular 4 to 14 wt %.

A dishwashing agent according to the invention, in particular an automatic dishwashing agent, wherein the copolymeric anionic polymer is selected from the group of the hydrophobically modified polycarboxylates and polysulfonates, is a particularly preferred subject matter, as the hydrophobic modification of the anionic copolymer can lead to an improvement of the rinsing and drying characteristics of the agent along with a lower formation of deposits.

The copolymers can possess two, three, four or a plurality of different monomer units.

Preferred copolymeric polysulfonates comprise, in addition to sulfonic acid group-containing monomer(s), at least one monomer from the group of the unsaturated carboxylic acids.

Unsaturated carboxylic acids of the formula $R^1(R^2)C=C(R^3)COOH$ are particularly preferably employed as the unsaturated carboxylic acid(s), in which $R^1$ to $R^3$ independently of one another stand for —H, —CH$_3$, a linear or branched, saturated alkyl group containing 2 to 12 carbon atoms, a linear or branched, mono or polyunsaturated alkenyl group containing 2 to 12 carbon atoms, alkyl or alkenyl groups substituted by —NH$_2$, —OH or —COOH as defined above or for —COOH or —COOR$^4$, wherein $R^4$ is a saturated or unsaturated, linear or branched hydrocarbon group containing 1 to 12 carbon atoms.

Particularly preferred unsaturated carboxylic acids are acrylic acid, methacrylic acid, ethacrylic acid, α-chloroacrylic acid, α-cyanoacrylic acid, crotonic acid, α-phenylacrylic acid, maleic acid, maleic anhydride, fumaric acid, itaconic acid, citraconic acid, methylenemalonic acid, sorbic acid, cinnamic acid or their mixtures. Of course, the unsaturated dicarboxylic acids can also be employed.

Copolymers of acrylic acid with methacrylic acid and of acrylic acid or methacrylic acid with maleic acid are inventively particularly preferably employed as the copolymeric polycarboxylates. Copolymers of acrylic acid with maleic acid which comprise 50 to 90 wt % acrylic acid and 50 to 10 wt % maleic acid, have proven to be particularly suitable. Their relative molecular weight, based on free acids, generally ranges from 2 000 to 70 000 g/mol, preferably 20 000 to 50 000 g/mol and especially 30 000 to 40 000 g/mol.

The molecular weights mentioned in the context of this publication are weight-average molecular weights $M_w$, which have been basically determined by means of gel permeation chromatography (GPC) using a UV detector. The measurement was carried out against an external standard, which by virtue of its structural similarity to the investigated polymers, provides realistic molecular weight values.

The preferred monomers that contain sulfonic acid groups are those of the formula $R^5(R^6)C=C(R^7)—X—SO_3H$ in which $R^5$ to $R^7$ independently of one another stand for —H, —$CH_3$, a linear or branched, saturated alkyl group containing 2 to 12 carbon atoms, a linear or branched, mono- or polyunsaturated alkenyl group containing 2 to 12 carbon atoms, alkyl or alkenyl groups substituted with —$NH_2$, —OH or —COOH or —COOH or —$COOR^4$, wherein $R^4$ is a saturated or unsaturated, linear or branched hydrocarbon group containing 1 to 12 carbon atoms, and X stands for an optionally present spacer group that is selected from —$(CH_2)_n$- with n=0 to 4, —COO—$(CH_2)_k$- with k=1 to 6, —C(O)—NH—C$(CH_3)_2$— and —C(O)—NH—CH($CH_2CH_3$)—.

Among these monomers those are preferred correspond to the formulas $H_2C=CH—X—SO_3H$ $H_2C=C(CH_3)—X—SO_3H$ $HO_3S—X—(R^6)C=C(R^7)—X—SO_3H$, in which $R^6$ and $R^7$ independently of one another are selected from —H, —$CH_3$, —$CH_2CH_3$, —$CH_2CH_2CH_3$, —$CH(CH_3)_2$ and X is an optionally present spacer group selected from —$(CH_2)_n$- with n=0 to 4, —COO—$(CH_2)_k$- with k=1 to 6, —C(O)—NH—C$(CH_3)_2$—, —C(O)—NH—C$(CH_3)_2$—$CH_2$— and —C(O)—NH—CH$(CH_3)$—$CH_2$—.

In this regard, particularly preferred sulfonic acid group-containing monomers are 1-acrylamido-1-propane sulfonic acid, 2-acrylamido-2-propane sulfonic acid, 2-acrylamido-2-methyl-1-propane sulfonic acid, 2-methacrylamido-2-methyl-1-propane sulfonic acid, 3-methacrylamido-2-hydroxypropane sulfonic acid, allyl sulfonic acid, methallyl sulfonic acid, allyloxybenzene sulfonic acid, methallyloxybenzene sulfonic acid, 2-hydroxy-3-(2-propenyloxy)propane sulfonic acid, 2-methyl-2-propene-1-sulfonic acid, styrene sulfonic acid, vinyl sulfonic acid, 3-sulfopropyl acrylate, 3-sulfopropyl methacrylate, sulfomethacrylamide, sulfomethylmethacrylamide and mixtures of the cited acids or of their water-soluble salts.

The sulfonic acid groups may be present completely or partly in neutralized form in the polymers, i.e. the acidic hydrogen atom of the sulfonic acid groups can be replaced, in some or all of the sulfonic acid groups, by metal ions, preferably alkali metal ions and in particular by sodium ions. Copolymers containing partly or fully neutralized sulfonic acid groups are inventively preferably employed.

In copolymers that comprise only monomers that contain carboxylic acid groups and monomers that contain sulfonic acid groups, the monomer distribution of the inventively preferably employed copolymers is preferably 5 to 95 wt % of each, the content of the monomer that contains sulfonic acid groups is particularly preferably 50 to 90 wt % and the content of the monomer that contains carboxylic acid groups is 10 to 50 wt %, the monomers being preferably selected from those cited above.

The molecular weight of the inventively preferably employed sulfo-copolymers can be varied to adapt the properties of the polymer to the desired application purpose. Preferred dishwashing agents, particularly automatic dishwashing agents are those wherein the copolymers have molecular weights from 2000 to 200 000 gmol$^{-1}$, preferably 4000 to 25 000 gmol$^{-1}$ and especially 5000 to 15 000 gmol$^{-1}$.

In another preferred embodiment, the copolymers, beside the carboxylic acid group-containing monomer and the sulfonic acid group-containing monomer, additionally contain at least one non-ionic, preferably hydrophobic monomer. In particular, the rinsing performance of the inventive automatic dishwashing agent was able to be improved by the addition of these hydrophobically modified polymers.

Inventively preferred dishwashing agents, particularly automatic dishwashing agents, are those wherein the dishwashing agent comprises a copolymer as the anionic copolymer, comprising
i) monomer(s) containing carboxylic acid groups
ii) monomer(s) containing sulfonic acid groups
iii) non-ionic monomer(s).

Monomers of the general Formula $R^1(R^2)C=(R^3)—X—R^4$ are preferably employed as the non-ionic monomers, in which $R^1$ to $R^3$ independently of one another stands for —H, —$CH_3$ or —$C_2H_5$, X stands for an optionally present spacer group selected from —$CH_2$—, —C(O)O— and —C(O)—NH—, and $R^4$ stands for a straight chain or branched saturated alkyl group containing 2 to 22 carbon atoms or for an unsaturated, preferably aromatic group containing 6 to 22 carbon atoms.

Particularly preferred non-ionic monomers are butene, isobutene, pentene, 3-methylbutene, 2-methylbutene, cyclopentene, hexene, 1-hexene, 2-methylpentene-1, 3-methylpentene-1, cyclohexene, methylcyclopentene, cycloheptene, methylcyclohexene, 2,4,4-trimethylpentene-1, 2,4,4-trimethylpentene-2, 2,3-dimethylhexene-1, 2,4-dimethylhexene-1, 2,5-dimethlyhexene-1, 3,5-dimethylhexene-1, 4,4-dimethylhexene-1, ethylcyclohexyne, 1-octene, α-olefins containing 10 or more carbon atoms such as for example 1-decene, 1-dodecene, 1-hexadecene, 1-octadecene and C22-α-olefin, 2-styrene, α-methylstyrene, 3-methylstyrene, 4-propylstyrene, 4-cyclohexylstyrene, 4-dodecylstyrene, 2-ethyl-4-benzylstyrene, 1-vinylnaphthalene, 2-vinylnaphthalene, methyl acrylate, ethyl acrylate, propyl acrylate, butyl acrylate, pentyl acrylate, hexyl acrylate, methyl methacrylate, N-(methyl)acrylamide, 2-ethylhexyl acrylate, 2-ethylhexyl methacrylate, N-(2-ethylhexyl)acrylamide, octyl acrylate, octyl methacrylate, N-(octyl)acrylamide, lauryl acrylate, lauryl methacrylate, N-(lauryl)acrylamide, stearyl acrylate, stearyl methacrylate, N-(stearyl)acrylamide, behenyl acrylate, behenyl methacrylate and N-(behenyl)acrylamide or their mixtures.

In another embodiment of the invention, a dishwashing agent according to the invention comprises at least one additional enzyme, in particular a protease, amylase, cellulase, pectin-cleaving enzyme, hemicellulase, mannanase, tannase, xylanase, xanthanase, β-glucosidase, carrageenase, perhydrolase, oxidase, oxidoreductase or a lipase, as well as combinations hereof, in particular a combination that is selected from protease and amylase, protease and lipase, protease and cellulase, protease and mannanase, amylase and lipase, amylase and cellulase, amylase and mannanase, lipase and cellulase, lipase and mannanase, lipase and cellulase, protease and amylase and lipase, protease and amylase and cellulase, protease and amylase and mannanase, amylase and lipase and cellulase, amylase and lipase and mannanase, lipase, cellulase and mannanase, protease and amylase and lipase and cellulase, protease and amylase and cellulase and mannanase.

Additional enzymes of this type are each advantageously comprised in the agent in a total amount of 1×10$^{-8}$ to 5 wt % based on the active protein. Each additional enzyme is comprised with increasing preference in agents according to the invention in an amount of 1×10$^{-7}$ to 3 wt %, 0.00001 to 1 wt %, 0.00005 to 0.5 wt %, 0.0001 to 0.1 wt % and particularly preferably 0.0001 to 0.05 wt %, based on active protein. In this regard, the active protein concentration can be determined in a customary manner for hydrolases for example by titrating the active centers in the presence of a suitable irreversible inhibitor and measuring the residual activity (see for example M. Bender et al., J. Am. Chem. Soc. 88, 24 (1966), pp. 5890-5913; the cited reference concerns proteases, wherein the principle of titration of the active centers is transferable to other hydrolases). The enzymes particularly preferably exhibit synergistic cleaning powers towards certain soils or stains, i.e. the enzymes comprised in the agent composition mutually support each other in their cleaning power. Such a synergy quite particularly preferably exists between the inventively comprised protease and another enzyme of an agent according to the invention, in particular between the inventively comprised protease and an amylase and/or a lipase and/or a mannanase and/or a cellulase and/or a pectin-cleaving enzyme. Synergistic effects can not only appear between various enzymes but also between one or more enzymes and additional ingredients of the agent according to the invention.

Preferred proteases are those of the subtilisin type. Examples of these are subtilisins BPN' and Carlsberg, the protease PB92, the subtilisins 147 and 309, the alkaline protease from Bacillus lentus, subtilisin DY and those enzymes of the subtilases no longer however classified in the stricter sense as subtilisins thermitase, proteinase K and the proteases TW3 and TW7. Subtilisin Carlsberg in further developed form is available under the trade name Alcalase® from Novozymes A/S, Bagsværd, Denmark. The subtilisins 147 and 309 are commercialized under the trade names Esperase® and Savinase® by the Novozymes company. The protease variants sold under the name BLAP® are derived from the protease from Bacillus lentus DSM 5483. Additional preferred proteases are furthermore for example the enzymes sold under the name PUR. Additional proteases are furthermore the enzymes available with the trade names Durazym®, Relase®, Everlase®, Nafizym®, Natalase®, Kannase® and Ovozyme® from the Novozymes Company, those under the trade names Purafect®, Purafect® OxP, Purafect® Prime, Excellase® and Properase® from Genencor, that under the trade name Protosol® from Advanced Biochemicals Ltd., Thane, India, that under the trade name Wuxi® from Wuxi Snyder Bioproducts Ltd., China, those under the trade names Proleather® and Protease P® from Amano Pharmaceuticals Ltd., Nagoya, Japan, and that under the designation Proteinase K-16 from Kao Corp., Tokyo, Japan. The proteases from Bacillus gibsonii and Bacillus pumilus which are disclosed in the international patent applications WO2008/086916 and WO2007/131656 are particularly preferably employed.

Examples of conditionable amylases according to the invention are the α-amylases from Bacillus licheniformis, from Bacillus amyloliquefaciens or from Bacillus stearothermophilus, as well as in particular their improved further developments for use in washing or cleaning agents. The enzyme from Bacillus licheniformis is available from the Novozymes Company under the name Termamyl® and from the Danisco/Genencor Company under the name Purastar®ST. Further development products of this α-amylase are available from the Novozymes Company under the trade names Duramyl® and Termamyl® ultra, from the Danisco/Genencor Company under the name Purastar® OxAm and from Daiwa Seiko Inc., Tokyo, Japan as Keistase®. The α-amylase from Bacillus amyloliquefaciens is commercialised by the Novozymes Company under the name BAN®, and derived variants from the α-amylase from Bacillus stearothermophilus under the names BSG® and Novamyl® also from the Novozymes Company. Moreover, for this purpose, attention should be drawn to the α-amylase from Bacillus sp. A 7-7 (DSM 12368) and the cyclodextrin-glucanotransferase (CGTase) from Bacillus agaradherens (DSM 9948). Fusion products of all the cited molecules can also be employed. Moreover, further developments of α-amylase from Aspergillus niger and A. oryzae available from the Company Novozymes under the trade name Fungamyl® are suitable. Additional commercial products that can be advantageously used are for example the Amylase-LT® and Stainzyme® or Stainzyme ultra® or Stainzyme plus®, the last also from the Novozymes company. Variants of these enzymes obtained by point mutations can also be inventively employed. Particularly preferred amylases are disclosed in the international applications WO 00/60060, WO 03/002711, WO 03/054177 and WO 07/079938, to which disclosures reference is therefore expressly made or in this regard their disclosed content is therefore expressly incorporated into the present patent application. Inventively conditionable amylases are moreover preferably α-amylases.

Exemplary inventively conditionable lipases or cutinases that are comprised in particular due to their triglyceride-cleaving activities, but also to generate peracids in situ from appropriate precursors, are the lipases that are originally obtainable from Humicola lanuginose (Thermomyces lanuginosus) or further developed lipases, especially those with the amino acid exchange D96L. They are commercialized, for example by the Novozymes Company under the trade names Lipolase®, Lipolase® Ultra, LipoPrime®, Lipozyme® and Lipex®.

Moreover, suitable cutinases, for example are those that were originally isolated from Fusarium solani pisi and Humicola insolens. Suitable lipases or cutinases whose starting enzymes were originally isolated from Pseudomonas mendocina and Fusarium solanii are for example available from Genencor Company. Further important commercial products that may be mentioned are the commercial preparations M1 Lipase® and Lipomax® originally from Gist-Brocades Company, and the commercial enzymes from the Meito Sangyo KK Company, Japan under the names Lipase MY-30®, Lipase OF® and Lipase PL® as well as the product Lumafast® from the Genencor Company.

Inventively conditionable cellulases (endoglucanases, EG) include for example the fungal, endoglucanase (EG)-rich cellulase preparation or its further developments that are offered by the Novozymes Company under the trade name Celluzyme®. The products Endolase® and Carezyme® based on the 50 kD-EG, respectively 43 kD-EG from Humicola insolens DSM 1800 are also obtainable from the Novozymes Company. Additional employable commercial products from this company are Cellusoft®, Renozyme® and Celluclean®. Cellulases, for example, which are available under the trade names Ecostone® and Biotouch® from AB Enzymes, Finland can also be used and which are at least partially based on the 20 kD-EG from Melanocarpus. Additional cellulases from the AB Enzymes Company are Econase® and Ecopulp®. Further suitable cellulases are from Bacillus sp. CBS 670.93 and CBS 669.93, the CBS 670.93 from Bacillus sp. being available under the trade name Puradax® from the Danisco/Genencor Company. Additional useable commercial products of the Danisco/Genencor Company are "Genencor detergent cellulase L" and lndiAge®Neutra.

Variants of these enzymes obtained by point mutations can also be inventively employed. Particularly preferred cellulases are Thielavia terrestris cellulase variants, which are disclosed in the international application WO 98/12307, cellulases from Melanocarpus, in particular Melanocarpus albomyces, which are disclosed in the international application WO 97/14804, cellulases of the EGIII type from Trichoderma reesei, which are disclosed in the European patent application EP 1 305 432 or variants that can be obtained from them, in particular those that are disclosed in the European patent applications EP 1240525 and EP 1305432, as well as cellulases, which are disclosed in the international patent applications WO 1992006165, WO 96/29397 and WO 02/099091. Reference is therefore expressly made to their respective disclosure or their disclosed content in this regard is therefore expressly incorporated into the present patent application.

In the context of the invention, pectin-cleaving enzymes (pectinases) are enzymes that cleave pectin and/or other galacturonanes. Pections are polysaccharides, whose major constituent is α-D-galacturonic acid as the monomer, preferably to at least 50 wt % and particularly preferably to at least 65 wt %. These galacturonic acid monomers are linked together though α-1,4-, sometimes also with a minor fraction through β-1,4-glycosidic bonds, and form the backbone of the pectin molecule that is periodically interrupted by 1,2-bonds with α-L-rhamnose. Consequently, pectin is a rhamno-galacturonic acid. Consequently, a pectin-cleaving enzyme is in particular an enzyme that catalyzes the hydrolysis of 1,4-α-D-galactosiduronic bonds.

Within the EC Classification of enzymes, in the numerical classification system for enzymes, the pectin-cleaving enzymes particularly belong to the enzyme classes (Enzyme Commission number) EC 3.1.1.1 1, EC 3.2.1.15, EC 3.2.1.67 and EC 3.2.1.82, and consequently fall into the third of the six major classes of enzymes, the hydrolases (E.C.3.-.-.-), sub-classification glycosylases (E.C. 3.2.-.-) and again sub-classification glycosidases (E.C. 3.2.1.-), i.e. enzymes that hydrolyse O- and/or S-glycosyl compounds. Consequently, pectin-cleaving enzymes are effective particularly against residues on dishes which comprise pectic acid and/or other galacturonanes, and catalyze their hydrolysis.

In the context of the present invention, the pectin-cleaving enzymes likewise include enzymes with the names pectinase, pectolyase, pectinesterase, pectindemethoxylase, pectinmethoxylase, pectinmethylesterase, pectase, pectinmethylesterase, pectinoesterase, pectinpectylhydrolase, pectindepolymerase, endopolygalacturonase, pectolase, pectinhydrolase, pectin-polygalacturonase, endo-polygalacturonase, poly-α-1,4-galacturonide glycanohydrolase, endogalacturonase, endo-D-galacturonase, galacturan 1,4-α-galacturonidase, exopolygalacturonase, poly(galacturonate) hydrolase, exo-D-galacturonase, exo-D-galacturonanase, exopoly-D-galacturonase, exo-poly-α-galacturonosidase, exo-polygalacturonosidase or exopolygalacturanosidase.

Exemplary suitable enzymes are available for example under the names Gamanase®, Pektinex AR®, X-Pect® or Pectaway® from Novozymes, under the name Rohapect UF®, Rohapect TPL®, Rohapect PTE100®, Rohapect MPE®, Rohapect MA plus HC, Rohapect DA12L®, Rohapect 10L®, Rohapect B1 L® from AB Enzymes and under the name Pyrolase® from Diversa Corp., San Diego, Calif., USA.

Additional enzymes, which are summarized under the term hemicellulases, can also be incorporated, especially for removing specific problematic soils. These include for example mannanases, xanthanlyases, xanthanases, xyloglucanases, xylanases, pullulanases and β-glucanases. β-Glucanase, extracted from Bacillus subtilis, is available under the name Cereflo® from the Novozymes Company. Hemicellulases that are inventively particularly preferred are mannanases, e.g. those that are marketed for example under the trade names Mannaway® from the Novozymes Company or Purabrite® from the Genencor Company.

To increase the bleaching action, a dishwashing agent according to the invention can also comprise oxidoreductases, for example oxidases, oxygenases, catalases (that react at lower $H_2O_2$ concentrations than peroxidase), peroxidases, such as halo-, chloro-, bromo-, lignin-, glucose- or manganese-peroxidases, dioxygenases or laccases (phenoloxidases, polyphenoloxidases). Suitable commercial products are Denilite® 1 and 2 from the Novozymes Company. For an advantageously employable exemplary system for an enzymatic perhydrolysis, reference may be made to the applications WO 98/45398 A1, WO 2005/056782 A2 and WO 2004/058961 A1. A combined enzymatic bleach system, containing an oxidase and a perhydrolase, is described in the application WO 2005/124012. Additional, preferably organic, particularly preferably aromatic compounds are advantageously added that interact with the enzymes to enhance the activity of the oxidoreductases in question (enhancers) or to facilitate the electron flow (mediators) between the oxidizing enzymes and the soils over strongly different redox potentials.

The inventively employable enzymes can also be conditioned together with concomitant substances, for example from the fermentation, or with stabilizers and be incorporated in a conditioned form of this type into a dishwashing agent according to the invention.

The above described active substance combinations are particularly suitable for removing bleachable soils, in particular tea stains, in dishwashing processes, in particular in automatic dishwashing processes.

Consequently, another subject matter of the invention is a method for removing stains, in particular tea stains, on hard surfaces, in particular dishes, said method comprising one of the procedural steps
  (a) contacting the hard surface with a cleaning liquor that comprises a dishwashing agent according to the invention, or
  (b) contacting the hard surface with a cleaning liquor that comprises a hydrogen peroxide source, a bleach catalyst and a protease, wherein the protease in a native electrophoresis in a polyacrylamide gel has a migration distance that is longer than the migration distance of the protease according to SEQ ID NO: 1.

This preferably concerns an automatic dishwashing process. The dishwashing agent is preferably dispensed into the interior of a dishwasher in the course of a dishwashing program, before the start of the main wash cycle or during the main wash cycle. The inventive agent can be manually dispensed or metered into the interior of the automatic dishwasher, but the agent is preferably metered into the interior of the automatic dishwasher by means of the metering chamber of the automatic dishwasher. Preferably, no additional water softener and no additional rinse agent is metered into the interior of the automatic dishwasher in the course of the cleaning process. This preferably concerns a method for removing bleachable soils.

All facts, subject matters and embodiments, which have been described for dishwashing agents according to the invention, are also applicable to inventive methods. Therefore, reference is hereby explicitly made to the disclosure at the appropriate location with the remark that this disclosure is also valid for the preceding method according to the invention.

Another subject matter of the invention is the use of a dishwashing agent according to the invention for removing stains, in particular tea stains, on hard surfaces, or of a protease that in a native electrophoresis in a polyacrylamide gel has a migration distance that is longer than the migration distance of the protease according to SEQ ID NO: 1, for removing stains, in particular tea stains, on hard surfaces in a cleaning liquor that additionally contains a hydrogen peroxide source and a bleach catalyst.

The use preferably relates to the removal of bleachable stains. All facts, subject matters and embodiments, which have been described for dishwashing agents according to the invention, respectively methods according to the invention, are also applicable to the cited methods. Therefore, reference is hereby explicitly made to the disclosure at the appropriate location with the remark that this disclosure is also valid for the preceding uses according to the invention.

EXAMPLES

Example 1

Determination of the Migration Distance of Proteases

The migration distance of four proteases was determined against the protease according to SEQ ID NO: 1 in a native polyacrylamide electrophoresis. The PHASTSystem from GE Healthcare was used for this. Polyacrylamide native "PhastGel Gradient 8-25" gels with a size of 43×50×0.45 mm were used as the separation gel, combined with a 0.112M Tris, 0.112M acetate (pH 6.4) buffer, whose native buffer strips of 3% agarose were upstream as the stacking gel with a size of 41×10×6 mm, combined with a 0.25M Tris, 0.88M L-alanine (pH 8.8) buffer. The separation was carried out following the instructions of the manufacturer as described in "PhastSystem Separation Technique File No. 120" (Amersham Biosciences 1998), but in the "reversed polarity electrode mode" for the separation of basic proteins. The electrophoresis was carried out until the protease bands had covered at least half of the available path length in the separation gel.

The investigated proteases and their migration distances are presented below in Table 1. The calculated isoelectric point at pH 7 and the calculated net charge at pH 7 are also listed for each protease. The isoelectric point and the net charge were calculated by means of the "Analysis" function of the BioAnnotater module of the software packet Vector NTI® Advance 10.3.0 (Invitrogen Corporation, 1600 Faraday Avenue, Carlsbad, Calif., USA) with the predefined standard (default) parameters.

TABLE 1

| | | Migration distance compared to the migration distance of the protease according to SEQ ID NO: 1 (indicated as a factor; n-fold) | Isoelectric point at pH 7 (calculated) | Net charge at pH 7 (calculated) |
|---|---|---|---|---|
| Protease 1 | Protease Ovozyme ® 64T (Novozymes) | 0.9 | 8.97 | 2.38 |
| Protease 2 | Performance improved variant F49 of the protease from *Bacillus lentus* according to WO 95/23221 | 0.9 | 8.97 | 2.38 |
| Protease 3 | Protease according to SEQ ID NO 2 | 1.2 | 9.69 | 5.38 |
| Protease 4 | Protease according to SEQ ID NO 3 | 1.1 | 9.52 | 4.38 |
| Protease reference | Protease according to SEQ ID NO 1 | 1 | 9.30 | 3.38 |

Example 2

Determination of the Cleaning Power of the Dishwashing Agents According to the Invention The cleaning power of a commercially available automatic dishwashing agent in the form of a dishwashing agent tablet was tested on tea stains; the tablet contained 15 wt % sodium percarbonate as the hydrogen peroxide source (bleaching agent), 0.03 wt % Mn-Me-TACN (Mn-TACN) as the bleach catalyst and 2.2 wt % TAED as the bleach activator, to which were added protease granulates with different proteases according to Example 1. The proteases were employed in amounts of equal total protein (0.056 g protease per wash cycle). The dishwashing process was carried out in the Miele G698SC dishwasher (program: 50° C., program duration 57 min, water hardness 21 (German hardness). The dishwashing agent tablet was placed in the dispensing device prior to the beginning of the cleaning program.

Triple determinations were carried out. Each experiment was counted and used to form the average value. The cleaning power was evaluated visually according to a scale of 1 to 10, wherein 10 was the best mark (no recognizable residue). The results are presented in the following Tables 2a (test series 1) and 2b (test series 2).

TABLE 2a

| Dishwashing agent tablet that comprises sodium percarbonate and Mn-TACN | Tea |
|---|---|
| Without protease | 6.5 |
| With protease 1 | 5.5 |
| With protease 2 | 5.8 |
| With protease 4 | 8.7 |

TABLE 2b

| Dishwashing agent tablet that comprises sodium percarbonate and Mn-TACN | Tea |
|---|---|
| Without protease | 5.1 |
| With protease 3 | 6.3 |

It is clear that the inventive dishwashing agents with the proteases 3 and 4 show a significantly improved (more than 1 mark) cleaning power on tea stains.

Example 3

Determination of the Cleaning Power of the Dishwashing Agents According to the Invention The cleaning power of a commercially available automatic dishwashing agent in the form of a dishwashing agent tablet was tested on tea stains; the tablet contained 15 wt % sodium percarbonate as the hydrogen peroxide source (bleaching agent), 2.2 wt % TAED as the bleach activator and 0.03 wt % Mn-Me-TACN (Mn-TACN) as the bleach catalyst, to which were added protease granulates with different proteases according to Example 1. The proteases were again employed in amounts of equal total protein (0.056 g protease per wash cycle). The additional composition of the dishwashing agent tablets corresponded to those of Example 2. The procedure and evaluation were carried out as described in Example 2. The results are presented below in Table 3.

TABLE 3

| Dishwashing agent tablet that contains sodium percarbonate | Tea |
|---|---|
| With protease 1 without Mn-TACN | 4.8 |
| With protease 1 with Mn-TACN | 5.7 |
| With protease 4 without Mn-TACN | 5.1 |
| With protease 4 with Mn-TACN | 9.1 |

It is again clear that the inventive dishwashing agents with the protease 4 with the bleach catalyst Mn-TACN show a significantly improved cleaning power on tea stains.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A dishwashing agent comprising a source of hydrogen peroxide comprising sodium percarbonate, a bleach catalyst and a protease, wherein the bleach catalyst comprises a complex of manganese with 1,4,7-trimethyl-1,4,7-triazacyclononane (Me-TACN), and wherein the protease has an amino acid sequence that is at least 98% identical to the amino acid sequence listed in SEQ ID NO. 2, wherein the agent exhibits improved cleaning on tea stains compared to an agent containing just the sodium percarbonate and bleach catalyst but not the protease.

2. The dishwashing agent according to claim 1, wherein the protease has an amino acid sequence identical to the amino acid sequence listed in SEQ ID NO. 2.

3. The dishwashing agent according to claim 1, wherein the agent comprises the hydrogen peroxide source in an amount of 2 to 30 wt. %, the bleach catalyst in an amount of 0.0025 to 1 wt. %, and the protease in an amount of $1 \times 10^{-8}$ to 10 wt. % based on the total protein content of the protease.

4. The dishwashing agent according to claim 1, wherein it is in solid form, a free flowing powder, a molded article, a liquid, a gel or a paste.

5. The dishwashing agent according to claim 1, comprising at least one additional ingredient that is selected from the group consisting of a builder, a surfactant, an anionic polymer, and combinations thereof, and further comprising at least one additional enzyme.

* * * * *

SEQUENCE LISTING

```
<160> NUMBER OF SEQ ID NOS: 3

<210> SEQ ID NO 1
<211> LENGTH: 269
<212> TYPE: PRT
<213> ORGANISM: Bacillus lentus

<400> SEQUENCE: 1

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175
```

```
Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 2
<211> LENGTH: 269
<212> TYPE: PRT
<213> ORGANISM: Bacillus sp.

<400> SEQUENCE: 2

Gln Gln Thr Val Pro Trp Gly Ile Thr Arg Val Gln Ala Pro Thr Val
1               5                   10                  15

His Asn Arg Gly Val Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265
```

```
<210> SEQ ID NO 3
<211> LENGTH: 269
<212> TYPE: PRT
<213> ORGANISM: Bacillus sp.

<400> SEQUENCE: 3

Ala Gln Ser Val Pro Trp Gly Ile Arg Arg Val Gln Ala Pro Thr Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Ala Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asp Gly Thr Ser Met Ala Thr Pro His Val Ala Gly Ala
    210                 215                 220

Ala Ala Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```